(12) United States Patent
Kappes et al.

(10) Patent No.: US 6,403,800 B1
(45) Date of Patent: Jun. 11, 2002

(54) SYNTHESIS OF 1-(2-SULFOETHYL)-PYRIDINIUM BETAINE

(75) Inventors: Elisabeth Kappes, Limburgerhof; Gregor Brodt, Heppenheim; Rudi Kröner, Mannheim; Norbert Wagner, Mutterstadt; Sören Hildebrandt, Speyer; Thomas Bogenstätter, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/600,874

(22) PCT Filed: Jan. 22, 1999

(86) PCT No.: PCT/EP99/00431

§ 371 (c)(1),
(2), (4) Date: Aug. 11, 2000

(87) PCT Pub. No.: WO99/41236

PCT Pub. Date: Aug. 19, 1999

(30) Foreign Application Priority Data

Feb. 11, 1998 (DE) .......................................... 198 05 487

(51) Int. Cl.⁷ ............................................. C07D 211/70
(52) U.S. Cl. ...................................................... 546/348
(58) Field of Search ......................................... 546/348

(56) References Cited

U.S. PATENT DOCUMENTS 3,131,189 A    4/1964   Klass

FOREIGN PATENT DOCUMENTS

| FR | 1529883 A | * | 5/1967 |
| WO | WO 91 16474 A | | 10/1991 |

OTHER PUBLICATIONS

Chemical Abstracts, vol. 71 (14) abst.No. 70507k, Oct. 6, 1969.*

Chemical Abstracts, vol. 72 (23) abst.No., 121,487j, Jun. 8, 1970.*

Chemical Abstracts, vol. 78 (23)abst.No. 146,881–v, Jun. 11, 1973.*

Le Berre, Andre, et al., "Addition of tertiary amine salts to electrophilic ethylenic compounds. II. Betaines and quaternary salts from. alpha., beta.–unsaturated acids" Bull. Soc. Chim. FR. (1973), (7–8) (PT. 2), 2404–8 CODEN: BSCFAS, XP002103472.

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

Described is a process for preparing 1-(2-sulfoethyl) pyridinium betaine wherein pyridine is reacted with a sulfoethylating agent from the group consisting of carbyl sulfate, ethionic acid and its salt and vinylsulfonic acid and vinylsulfonate, the reaction taking place in aqueous solution or in pyridine.

9 Claims, No Drawings

SYNTHESIS OF 1-(2-SULFOETHYL)-PYRIDINIUM BETAINE

This application is a 371 of PCT/EP99/00431, filed Jan. 22, 1999. The invention relates to the preparation of 1-(2-sulfoethyl)pyridinium betaine.

1-(2-Sulfoethyl)pyridinium betaine (PES) belongs to the class of compound constituted by the sulfobetaines. These comprise inner salts (=zwitterionic compounds) in which the positive charge is on the nitrogen atom and the negative charge is on the sulfonate group. PES plays an important part, for example, as a secondary brightener in the electrolytic deposition of nickel.

WO 91/16474 describes the use of PES as secondary brighteners in the deposition of nickel from acidic nickel baths. Secondary brighteners are used to level rough surfaces, as obtained in the deposition of nickel from nickel electrolytes, without embrittling the deposit. For enhancing the quality of nickel coatings they are almost always employed together with one or more substratum brighteners, which produce a bright rather than a matt nickel deposit.

The preparation of PES has already been described in the literature.

U.S. Pat. No. 3,131,189 discloses the synthesis of quaternary ammonium betaine salts from carbyl sulfate or derivatives of carbyl sulfate and tertiary amines. Described inter alia is the synthesis of PES from pyridine and carbyl sulfate at room temperature in dichloroethane.

*J. Org. Chem.* 29 (1964) 2489 also describes the reaction of carbyl sulfate with pyridine in dichloroethane. Here, PES is obtained in 60% yield.

In the processes according to the two aforementioned publications, however, the batch sizes realized are small, in the region of approximately 5 g of PES. A further disadvantage is the use of organic solvents such as dichloroethane, which has been reported to be carcinogenic in animal experiments.

A further, two-stage synthesis of PES is treated in *J. Org. Chem.* 26 (1961) 4520. In the first step, pyridine is reacted with 1,2-dibromoethane to form a bromoethyl-substituted pyridinium bromide which is reacted with addition of sodium sulfite to give PES.

FR-B 2 270 241 describes a process for sulfoethylating tertiary amines using aliphatic esters of ethenesulfonic acid as sulfonating agents. The products are the sulfoethyl betaines of the tertiary amines. Here, yields of up to 95% for PES are achieved. A disadvantage is the use of the vinylsulfonic esters, which are more expensive than vinylsulfonic acid. These esters must first be prepared by esterifying the corresponding acid with alkyl orthoformates, chloroformates or alkyl chlorosulfites or, as described in H. Distler, Angew. Chem. 77 (1965) 291, by reacting alkoxides with β-chloroethanesulfonyl chloride. A further disadvantage is the production in stoichiometric amounts of the ester alcohol as a waste product.

Bull. Soc. Chim. Fr. 1973, 7–8, 2404 describes the formation of sulfobetaines, and including PES, from ethenesulfonic acid and/or its salt and tertiary amines. The synthesis of PES starting from ethenesulfonic acid is termed difficult. Heating of the solvent-free salt pyridinium vinylsulfonate at not more than 150° C. makes it possible to obtain PES in trace amounts. A slightly more successful conversion, albeit a very slow one, is achieved by reacting pyridine with vinylsulfonate in boiling acetic acid.

U.S. Pat. No. 3,275,672 relates to a process for manufacturing esters of sulfonic acid, preferably esters of vinylsulfonic acid. The manufacturing results from reacting carbyl sulfate with an alkanol.

It is an object of the invention to provide a cost effective industrially relevant synthesis for PES. A further object, resulting from the abovementioned solvent-free salt pyridinium vinylsulfonate at not more than 150° C. makes it possible to obtain PES in trace amounts. A slightly more successful conversion, albeit a very slow on, is acheived by reacting pyridine with vinylsulfonate in boiling acetic acid.

It is an object of the invention to provide a cost-effective industrially relevant synthesis for PES. A further object, resulting from the abovementioned disadvantages, is to avoid the use of chlorinated organic solvents, which may be carcinogenic.

In accordance with the invention, this object is achieved by a process for preparing PES which comprises reacting pyridine with a sulfoethylating agent from the group consisting of carbyl sulfate, ethionic acid and its salt and vinylsulfonic acid and vinylsulfonate and in aqueous solution or in pyridine.

The process of the invention provides a cost-effective synthesis which is practicable on the industrial scale. It is possible to avoid the use of expensive chlorinated organic solvents which may be carcinogenic, and the synthesis may be conducted as a "one-pot" reaction, i.e., in one step, without isolation of intermediates.

In one embodiment of the invention, the PES may be prepared by reacting pyridine with a sulfoethylating agent from the group consisting of carbyl sulfate, ethionic acid and its salt and vinylsulfonic acid and vinylsulfonate in aqueous solution.

An aqueous solution in this context is a reaction mixture containing at least 20% by weight, preferably between 20% by weight and 80% by weight, with particular preference between 30% by weight and 70% by weight, with very particular preference 45% by weight and 65% by weight, water.

When conducting the reaction in aqueous solution, a pH in the range from 1.0 to 11.0, preferably from 4.0 to 9.0, with particular preference from 5.0 to 8.0, is generally observed, this pH being established with acid, preferably sulfuric acid, or aqueous alkali metal hydroxide solution. Fluctuations in the pH of approximately ±2 within the stated upper and lower limits are possible.

The sulfoethylating agent is mixed with pyridine in a molar ratio of from 1:0.1 to 1:3, preferably from 1:0.5 to 1:2, with particular preference from 1:0.6 to 1:1. The mixture is heated, generally with stirring, at from 20 to 250° C., preferably from 80 to 160° C., with particular preference from 130 to 160° C. The pressure is generally from 1 atm to 200 atm, preferably from 1 atm to 50 atm, with particular preference from 2 atm to 10 atm. With very particular preference, the reaction is conducted under an autogenous pressure of from about 3 atm to 8 atm in an autoclave.

Depending on the chosen conditions, the reaction time is between 3 and 40 hours, preferably between 4 and 20 hours.

The reaction product obtained is a water-clear to brownish aqueous solution containing PES and alkali metal sulfate. If an acid other than sulfuric acid is used to adjust the pH, then the solution contains the salt corresponding to the acid rather than alkali metal sulfate. In addition, unreacted sulfoethylating agent and pyridine may be present. Depending on the chosen starting materials and reaction conditions, further by-products may be present, such as any by-product from the synthesis of the sulfoethylating agent, and any hydrolysis products that may have formed during the reaction.

The salt obtained depending on reaction conditions may be removed at least partly from the aqueous product solution by means of process steps which are general knowledge. For instance, the amount of alkali metal sulfate in the aqueous product solutions may be reduced, for example, by cooling and subsequent filtration. The vinylsulfonate which remains if conversion is incomplete may in general remain in the solution, for subsequent use of PES as a secondary brightener; unreacted pyridine may be removed by steam distillation and, if appropriate, may be used again in subsequent batches. The PES solution may be converted to a solid form by methods which are, in general, known, an example being spray drying. Similarly, PES may be isolated from these solutions with the aid of methods that are known to the skilled worker.

When carbyl sulfate is used as sulfoethylating agent in aqueous solution, a first process step in addition to those described above is to react carbyl sulfate with 10–50% strength by weight alkali metal hydroxide solution at from 10 to 70° C. in a reaction which is known from EP-B-0 054 142. During the addition of carbyl sulfate, it is preferred to observe a pH of greater than or equal to 7 and a temperature of less than or equal to 50° C.

Following the addition of carbyl sulfate, the reaction mixture is heated as described above, the pH being held initially at more than 7.0, preferably more than 9.0, using aqueous alkali metal hydroxide solution, after which acid is added to establish a pH of from 1.0 to 9.0, preferably from 4.0 to 8.5, with particular preference from 5.0 to 8.0. Fluctuations in the pH of approximately ±2 within the stated upper and lower limits are possible.

The subsequent synthesis takes place under the reaction conditions described above. It is unimportant in this context whether the pyridine is added at the beginning of the reaction or after the reaction of carbyl sulfate and alkali metal hydroxide solution.

In the course of this reaction, the reaction may proceed along the following pathways, individually or alongside one another:

a) the direct formation of PES from carbyl sulfate;
b) the formation of ethionic acid and/or its salt from carbyl sulfate, which reacts to PES in situ directly or by way of vinylsulfonate formed from the ethionic acid and/or its salt;
c) the formation of vinylsulfonate from carbyl sulfate, which is reacted to PES in situ.

The compounds formed as intermediates in the reaction of carbyl sulfate and pyridine under the reaction conditions of the invention, such as vinylsulfonic acid or vinylsulfonate and ethionic acid and/or its salt, may also be used directly as sulfoethylating agent in the synthesis of PES under the reaction conditions described above. In this case, vinylsulfonic acid and/or vinylsulfonate and ethionic acid and/or its salt may be obtained not only from carbyl sulfate but also from other starting materials. Vinylsulfonate may be obtained, for example, by reacting ethanol and sulfur trioxide, as known from J. Am. Chem. Soc. 76 (1954) 5361 and U.S. Pat. No. 3,637,793. In the reaction, ethionic acid occurs as an intermediate.

It is particularly preferred to use vinylsulfonate as sulfoethylating agent. Preference is given to the use of the industrially obtainable sodium salt of vinylsulfonic acid, with particular preference in the form of an aqueous solution with a concentration of 10–40% by weight, with very particular preference 25–30% by weight.

An industrially obtainable solution of the sodium salt of vinylsulfonic acid refers in this context to the solution including customary by-products.

The pH is adjusted by adding acid, preferably one equivalent, to a value in the range from 1.0 to 9.0, preferably from 4.0 to 9.0, with particular preference from 5.0 to 8.0, and is maintained during the reaction by adding acid continuously or in portions. Furthermore, the required amount of acid may be added in one portion. Fluctuations in the pH of approximately ±2 within the stated upper and lower limits are possible. Particular preference is given to pH-regulated metering of the acid.

The acid used is preferably sulfuric acid. An alternative possibility is to use a weak acid, preferably aqueous acetic acid, as solvent. In that case additional metering of the acid, and pH regulation, are necessary. The subsequent reaction takes place under the reaction conditions described above.

A further alternative is the use of anhydrous acetic acid as solvent when conducting the reaction under autogenous pressure at a temperature above the boiling point of acetic acid, preferably at from 130° C. to 160° C. Additional metering of acid, and pH regulation, are unnecessary.

It is possible to add polymerization inhibitors in order to prevent polymerization of the vinylsulfonate.

Alternatively to the preparation of PES by reacting pyridine with a sulfoethylating agent from the group consisting of carbyl sulfate, ethionic acid and its salt and vinylsulfonic acid and vinylsulfonate in aqueous solution, this reaction may be conducted in pyridine or another organic solvent. In the case of this reaction, the sulfoethylating agent used is preferably carbyl sulfate.

In this case, the pyridine is generally added in an excess of not more than 50 times relative to the sulfoethylating agent, preferably in an excess of not more than 25 times.

The reaction is conducted, generally with stirring, at a temperature from 20° C. to 250° C., preferably from 80° C. to 160° C., with particular preference from 130° C. to 160° C., under a pressure of from 1 atm to 200 atm, preferably from 1 atm to 50 atm, with particular preference from 1 atm to 10 atm. Very particular preference is given to a reaction at a temperature of 150° C. under an autogenous pressure of from approximately 2 atm to 4 atm in an autoclave.

Excess pyridine may be removed after the reaction by distillation and, if appropriate, used again in subsequent reactions.

The examples which follow further elucidate the invention.

EXAMPLE 1

520 g of 25% strength by weight aqueous technical-grade vinylsulfonate solution and 79 g of pyridine are adjusted to a pH of 5.9 with 96% strength by weight sulfuric acid and are heated to 150° C. under the autogenous pressure with stirring. Approximately 39 g of 96% strength by weight sulfuric acid are added continuously so that the pH is from 7.5 to 5.0 (measured at room temperature). After 10 hours, an aqueous solution is obtained which contains 150 g of PES, 26 g of unreacted vinylsulfonate and 56.8 g of sodium sulfate. Also present, to a minor extent, are by-products from the industrial synthesis of vinylsulfonate. Unreacted pyridine is removed by steam distillation and is available for subsequent reactions.

EXAMPLE 2

79 g of pyridine, 200 g of 50% strength by weight aqueous NaOH solution and 188 g of carbyl sulfate (in pieces or melted) are introduced into 210 g of water (NB: exothermic reaction) and adjusted if appropriate to a pH of more than 9 using NaOH. During the addition of carbyl sulfate, the pH should not go below 7.0 and the temperature should not go above 50° C. The batch is heated in an autoclave at from 145° C. to 150° C. under autogenous pressure and is subsequently adjusted to a pH of from 5.0 to 7.5 by adding 96% strength by weight sulfuric acid. After approximately 10 hours, a solution is obtained which contains 140 g of PES, 17.5 g of disodium ethionate, 23.4 g of vinylsulfonate and 170 g of sodium sulfate.

EXAMPLE 3

520 g of 25% strength by weight aqueous technical-grade vinylsulfonate solution and 63.2 g of pyridine are heated to 145° C. under autogenous pressure with stirring. The mixture is adjusted to a pH of from 7.5 to 5.0 using 96% strength by weight sulfuric acid. After approximately 7 hours, an aqueous solution is obtained whose principal components comprise 142 g of PES, 31.2 g of vinylsulfonate and about 54 g of sodium sulfate. If the technical-grade vinylsulfonate solution used already includes sodium sulfate, then the sulfate level found increases accordingly. Unreacted pyridine is removed by steam distillation and is available for subsequent reactions. The resulting solution is cooled to below 10° C., and precipitated sodium sulfate is removed by filtration.

EXAMPLE 4

13.0 g of the sodium salt of vinylsulfonic acid and 7.9 g of pyridine are admixed with 100 ml of glacial acetic acid and heated at 160° C. under autogenous pressure. After 50 hours, 93% of the vinylsulfonate have undergone conversion to PES.

We claim:

1. A process for preparing 1-(2-sulfoethyl)pyridinium betaine (PES), comprising:

reacting pyridine with a sulfoethylating agent selected from the group consisting of carbyl sulfate, ethionic acid, salt of ethionic acid, vinylsulfonic acid, vinylsulfonate, and a mixture thereof, the reaction taking place:
   in aqueous solution which comprises at least 20% by weight water and having a pH of 1.0 to 11.0 established by sulfuric acid; or
   in pyridine.

2. A process as claimed in claim 1, wherein pyridine and the sulfoethylating agent are reacted in a molar ratio of from 0.1:1 to 3:1.

3. A process as claimed in claim 1, wherein the pH is adjusted to from 1.0 to 11.0 and is maintained within this range during the reaction.

4. A process as claimed in claim 1, wherein the reaction takes place at a temperature of from 20° C. to 250° C. under a pressure of from 1 atm to 200 atm.

5. A process as claimed in claim 1, wherein carbyl sulfate is used as sulfoethylating agent.

6. A process as claimed in claim 1, wherein ethionic acid and/or its salt is used as sulfoethylating agent.

7. A process as claimed in claim 1, wherein vinylsulfonic acid and/or vinylsulfonate is used as sulfoethylating agent.

8. A process as claimed in claim 7, wherein vinylsulfonate is used in the form of an industrially obtainable solution of the sodium salt of vinylsulfonic acid with a concentration of from 10 to 40% by weight.

9. A process as claimed in claim 1, wherein the sulffiric acid is added in one portion.

* * * * *